United States Patent [19]

Goto et al.

[11] 4,444,786
[45] Apr. 24, 1984

[54] CARBAMATE DERIVATIVES, INSECTICIDAL, MITICIDAL OR NEMATOCIDAL COMPOSITIONS CONTAINING THE SAME, AND PROCESS FOR PREPARING THE SAME

[75] Inventors: Takeshi Goto; Hisashi Takao; Norio Yasudomi; Norio Osaki; Tadateru Murata, all of Tokushima, Japan

[73] Assignee: Otsuka Chemical Co., Ltd., Osaka, Japan

[21] Appl. No.: 352,927

[22] Filed: Feb. 26, 1982

[30] Foreign Application Priority Data

Nov. 27, 1981 [JP] Japan ................................ 56-189989

[51] Int. Cl.$^3$ ..................... A01N 37/52; C07C 119/18
[52] U.S. Cl. .................................. 424/298; 260/453.3
[58] Field of Search ...................... 260/453.3; 424/298

[56]  References Cited
U.S. PATENT DOCUMENTS 4,323,578  4/1982  Middleton ........................ 260/453.3

Primary Examiner—Henry R. Jiles
Assistant Examiner—Robert C. Whittenbaugh

Attorney, Agent, or Firm—Sughrue, Mion, Zinn, Macpeak, and Seas

[57] ABSTRACT

A novel S-methyl N-[{N-methyl-N-(N,N-disubstituted aminosulfenyl)carbamoyl}oxy]thioacetamidate derivative represented by the formula (I):

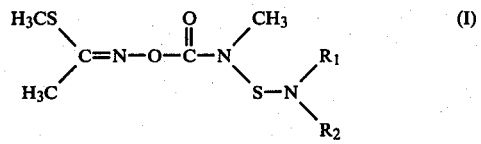

which has insecticidal, miticidal or nematocidal activity comparable to or higher than known methomyl but which is quite low in toxicity to warm-blooded animals as compared to methomyl, is disclosed. An insecticidal, miticidal or nematocidal composition containing the same, and a process for preparing the same are also disclosed. A method for controlling noxious insects, mites or nematodes by using the same is further disclosed.

3 Claims, No Drawings

CARBAMATE DERIVATIVES, INSECTICIDAL, MITICIDAL OR NEMATOCIDAL COMPOSITIONS CONTAINING THE SAME, AND PROCESS FOR PREPARING THE SAME

BACKGROUND OF THE INVENTION

This invention relates to a novel S-methyl N-[{N-methyl-N-(N,N-disubstituted aminosulfenyl)carbamoyl}-oxy]thioacetamidate derivative, an insecticidal, miticidal or nematocidal composition containing the derivative as an active ingredient, a process for preparing such a derivative, and a method for controlling noxious insects, mites or nematodes. In the present specification, the term "insecticidal" includes "miticidal" and "nematocidal" in addition to "insecticidal," and the term "insect(s)" includes "mite(s)" and "nematode(s)" in addition to "insect(s)", respectively, unless otherwise indicated.

FIELD OF THE INVENTION

It is known that some carbamate compounds have high insecticidal activity, and they include those actually in use. However, many of such carbamate compounds have the drawback of being toxic to warm-blooded animals. Above all, S-methyl N-[(methylcarbamoyl)oxy]thioacetamidate (hereinafter referred to as "methomyl," as generally called) is known to have high insecticidal activity, but it causes problems in practical use due to high toxicity to warm-blooded animals. Accordingly, if it is possible to prepare carbamate compounds which are comparable to methomyl in insecticidal activity and yet have reduced toxicity to warm-blooded animals, the compounds should be very useful.

From such viewpoints, various methomyl sulfenyl compounds have been synthesized, and the relation between their insecticidal activity and toxicity to warm-blooded animals is being investigated, with reports made on the results of investigations. For example, Belgian Pat. No. 848,912 discloses N,N'-bis-[1-methyl-thioacetaldehyde-O-(N-methylcarbamoyl)oxyimino]-sulfide, and Japanese Patent Application (OPI) No. 76835/74 (the term "OPI" used herein means an unexamined Japanese publication) discloses S-methyl N-[{N-methyl-N-(N-methyl-N-benzenesulfonylaminosulfenyl)carbamoyl}oxy]thioacetamidate. These methomyl sulfenyl compounds nevertheless fail to fully fulfill the requirements in respect to insecticidal activity, toxicity to warm-blooded animals and to fish and manufacturing process.

SUMMARY OF THE INVENTION

As the result of intensive research in an attempt to develop methomyl sulfenyl compounds which will fulfill all of such requirements, it has been found that the contemplated objects can be achieved by compounds represented by the formula (I):

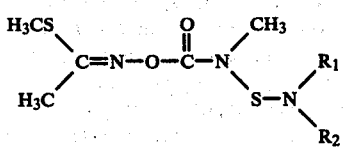

wherein $R_1$ and $R_2$, which may be the same or different, each represents $-X-COOR_3$, in which X represents an alkylene group having 1 to 6 carbon atoms, and $R_3$ represents an alkyl group having 1 to 8 carbon atoms or a cycloalkyl group having 3 to 6 carbon atoms; and $R_2$ further represents an alkyl group having 1 to 8 carbon atoms; a cycloalkyl group having 3 to 6 carbon atoms; a phenyl group which may be substituted with a halogen atom, an alkyl group having 1 to 3 carbon atoms or an alkoxy group having 1 to 3 carbon atoms; a benzyl group which may be substituted with a halogen atom, an alkyl group having 1 to 3 carbon atoms or an alkoxy group having 1 to 3 carbon atoms; or $-Z-R_4$, in which Z represents a carbonyl group or a sulfonyl group, and $R_4$ represents an alkyl group having 1 to 3 carbon atoms, an alkoxy group having 1 to 3 carbon atoms or a phenyl group which may be substituted with a lower alkyl group.

In the definition for the formula (I) above, the alkyl moiety in the alkyl group, alkylene group and alkoxy group may be straight chain or branched chain.

Thus, this invention has been accomplished.

DETAILED DESCRIPTION OF THE INVENTION

The S-methyl N-[{N-methyl-N-(N,N-disubstituted aminosulfenyl)carbamoyl}oxy]thioacetamidate derivatives of the formula (I) are novel compounds which have not been disclosed in any literature and which have been discovered by the present inventors for the first time. It has been found that the compounds of the formula (I) have outstanding insecticidal activity or controlling effect on agricultural and forestry noxious insects and household noxious insects and are comparable to or higher than methomyl which has the highest insecticidal activity heretofore known, in such effect. The compounds of the formula (I) are effective on a wide variety of noxious insects, mites and nematodes which are harmful to vegetables, trees, other plants and man, such as Hemiptera, Lepidoptera, Coleoptera, Diptera, Thysanoptera, Orthoptera, Isopoda, Acarina, Tylenchida, etc. Examples of these insects, mites and nematodes are as follows.

Hemiptera (1) Deltocephalidae: *Nephotettix cincticeps*
(2) Delphacidae: *Laodelphax striatellus, Nilaparvata lugens,*
(3) Aphididae: *Myzus persicae, Aphis gossypii*
(4) Pentatomidae: *Nezara antennata, Nezara viridula.*

Lepidoptera (1) Noctuidae: *Spodoptera litura, Agrotis segetum, Spodoptera exigua,*
(2) Tortricidae: *Adoxophyes orana*
(3) Pyralidae: *Chilo suppressalis, Ostrinia furnacalis, Cnaphalocrocis medinalis,*
(4) Plutellidae: *Plutella xylostella*

Coleoptera (1) Curculionidae: *Echinocnemus squameus, Lissorhoptrus oryzophilus,*
(2) Scarabaeidae: *Popillia japonica*
(3) Coccinellidae: *Henosephilachna vigintioctopunctata,*

Diptera (1) Muscidae: *Musca domestica,*
(2) Cecidomyiidae: *Aspondylia sp.*
(3) Agromyzidae: *Liriomyza chinensis,*

Thysanoptera

Thripidae: *Thrips tabaci, Scirtothrips dorsalis,*

Orthoptera

Gryllotalpidae: *Gryllotalpa africana*

Isopoda

Armadillidae: *Armadillidium vulgare*

Acarina

Tetranychidae: *Tetranychus cinnabarinus, Tetranychus urticae, Panonychus citri,*

Tylenchida

Heteroderidae: Meloidogyne incognita

The toxicity of the compounds of the formula (I) to warm-blooded animals is as low as about 1/5 to about 1/50 the toxicity of methomyl. The present compounds exhibit insecticidal activity or controlling effect on the above-described organisms in any stage or a specific stage of their growth and are therefore effectively usable for controlling them in the fields of agriculture, forestry and sanitation.

The present compounds of the formula (I) are very easy to prepare with high purities in high yields and have great commercial advantages as will be described in detail later.

Typical of the compounds of the formula (I) are listed below. This invention is, however, not limited thereto.

S-Methyl N-[{N-Methyl-N-(N-methyl-N-ethoxycarbonylmethylaminosulfenyl)carbamoyl}oxy]thioacetamidate S-Methyl N-[{N-Methyl-N-(N-n-butyl-N-methoxycarbonylmethylaminosulfenyl)carbamoyl}oxy]thioacetamidate S-Methyl N-[{N-Methyl-N-(N-phenyl-N-ethoxycarbonylmethylaminosulfenyl)carbamoyl}oxy]thioacetamidate S-Methyl N-[{N-Methyl-N-(N-benzoyl-N-ethoxycarbonylmethylaminosulfenyl)carbamoyl}oxy]thioacetamidate S-Methyl N-[{N-Methyl-N-(N-n-propyl-N-ethoxycarbonylethylaminosulfenyl)carbamoyl}oxy]thioacetamidate S-Methyl N-[{N-Methyl-N-(N-isopropyl-N-ethoxycarbonylethylaminosulfenyl)carbamoyl}oxy]thioacetamidate S-Methyl N-[{N-Methyl-N-(N-n-butyl-N-ethoxycarbonylethylaminosulfenyl)carbamoyl}oxy]thioacetamidate S-Methyl N-[{N-Methyl-N-(N-ethoxycarbonyl-N-ethoxycarbonylethylaminosulfenyl)carbamoyl}oxy]thioacetamidate S-Methyl N-[{N-Methyl-N-(N,N-bis(ethoxycarbonylmethyl)aminosulfenyl)carbamoyl}oxy]thioacetamidate S-Methyl N-[{N-Methyl-N-(N,N-bis(ethoxycarbonylethyl)aminosulfenyl)carbamoyl}oxy]thioacetamidate The compounds of the formula (I) can be prepared, for example, by reacting S-methyl N-[{methylcarbamoyl}oxy]thioacetamidate represented by the formula (II):

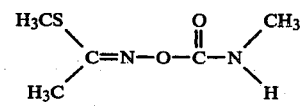

with an aminosulfenyl chloride derivative represented by the formula (III):

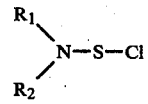

wherein $R_1$ and $R_2$ are as defined above.

The reaction of the compound of the formula (II) and the compound of the formula (III) can be conducted in the presence or absence of a solvent. Examples of the solvent which can be used include halogenated hydrocarbons such as methylene chloride, chloroform, carbon tetrachloride, etc.; and ethers such as diethyl ether, dibutyl ether, tetrahydrofuran, dioxane, etc. The proportions of the compound of the formula (II) and the compound of the formula (III) are not particularly limited but are widely variable suitably. Usually about 1 to about 1.5 moles, preferably 1 to 1.1 moles, of the latter is used per mole of the former. Preferably the reaction is conducted in the presence of a basic compound. Examples of the basic compound which can be used include tertiary amines such as triethylamine, tributylamine, dimethylaniline, diethylaniline, ethylmorpholine, etc.; and pyridines such as pyridine, picoline, lutidine, etc. The basic compound can be used in an amount sufficient to capture the hydrogen chloride to be produced by the reaction as a by-product. Usually about 1 to about 2 moles, preferably 1 to 1.5 moles, of the basic compound is used per mole of the compound of the formula (II). The reaction, which proceeds with cooling, at room temperature or with heating, is carried out usually at about $-70°$ to about 70° C., preferably $-10°$ to about 30° C. The reaction time varies depending upon the basic compound used, but usually is about 1 to about 30 hours.

The compound of the formula (I) thus-obtained can be easily isolated and purified by a usual method of separation, such as solvent extraction, recrystallization or column chromatography.

The compound of the formula (I) of this invention can be formulated into an emulsion, wettable powder, suspension, concentrated suspension, granule, fine particle, pellet, dust, coating composition, foam spray, aerosol, microcapsule composition, impregnant to be applied to a natural or synthetic material, fumigant, concentrated preparation to be applied in a small amount, etc.

Various surfactants are usable for the preparations of such emulsions, dispersions, suspensions and foams. Examples of the surfactant which can be used include nonionic surfactants such as polyoxyethylene alkylphenol ethers, polyoxyethylene alkyl ethers, polyoxyethylene alkyl esters, polyoxyethylene sorbitan alkyl esters, sorbitan alkyl esters, etc.; and anionic surfactants are alkylbenzenesulfonates, alkyl sulfosuccinates, alkyl sulfates, polyoxyethylene alkylether sulfates, alkylnaphthalene sulfonates, lignin sulfonates, etc.

Solvents, diluting agents and carriers for the present compounds include various organic solvents, aerosol propellants, natural minerals, vegetables, synthetic compounds, binders, etc. Examples of preferred organic solvents are benzene, toluene, xylene, ethylbenzene, chlorobenzene, alkylnaphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, fractions of mineral oils. Examples of useful aerosol propellants are propane, butane, halogenated hydrocarbons, nitrogen, carbon dioxide, etc. Examples of useful natural minerals are kaolin, talc, bentonite, diatomaceous earth, clay, montmorillonite, chalk, calcite, pumice, dolomite, etc. Examples of useful vegetables are coconut shells, tobacco stalks, sawdust, etc. Examples of useful synthetic compounds are alumina, silicates, sugar polymers, etc. Examples of useful binders are carboxymethyl cellulose, gum arabic, polyvinyl alcohol, polyvinyl acetate, etc. The preparations can be colored with organic or inorganic dyes.

The compounds of the formula (I) of this invention are formulated into various preparations, such as those exemplified above, so that the preparations contain, as an active ingredient, an insecticidally, miticidally or nematocidally effective amount (e.g., about 0.1 to about 95% by weight, preferably about 0.5 to about 90% by weight) of the compound. Depending on the application contemplated, such preparations are used as such, or as diluted with a carrier or water.

The present invention will be described below in greater detail with reference to the following examples.

EXAMPLE 1

Preparation of S-methyl N-[{N-methyl-N-(N-isopropyl-N-ethoxycarbonylethylaminosulfenyl)carbamoyl}oxy]thioacetamidate To 50 ml of methylene chloride was added 8.1 g (0.05 mole) of S-methyl N-[(methylcarbamoyl)oxy]thioacetamidate and 11.3 g (0.05 mole) of N-isopropyl-N-ethoxycarbonylethylaminosulfenyl chloride, and the mixture was cooled at 0° to 5° C. 6 g (0.06 mole) of triethylamine was dropwise added thereto at the same temperature, and the resulting mixture was stirred for 2 hours. After completion of the reaction, the reaction solution was washed successively with water, diluted hydrochloric acid and water, and the methylene chloride layer was dried and concentrated. To the concentrated residue was added diethyl ether, and crystals were filtered off. Then, the ethereal layer was concentrated to obtain an oily product. Yield: 12.5 g (71.2%).

For the identification of the product, a portion thereof was purified by silica gel column chromatography, using benzene/ethyl acetate (4:1) as the elution solvent, whereby an oily product was obtained.

Elemental Analysis:

|  | C | H | N |
|---|---|---|---|
| Found (%) | 44.55 | 7.04 | 12.09 |
| Calcd. for $C_{13}H_{25}N_3O_4S_2$ (molecular wt. 351.499) | 44.42 | 7.17 | 11.96 |

NMR in $CDCl_3$:
$\delta$1.17 ppm (d, 6H), $\delta$1.21 ppm (t, 3H),
$\delta$2.29 ppm (s, 3H), $\delta$2.42 ppm (s, 3H),
$\delta$2.68 ppm (t, 2H), $\delta$3.0–3.7 ppm (m, 3H),
$\delta$3.38 ppm (s, 3H), $\delta$4.08 ppm (q, 2H).

Thus, the product was confirmed to have the following formula:

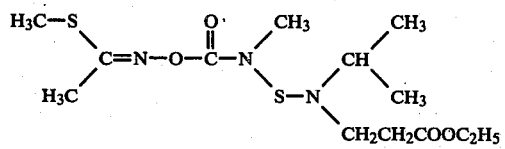

EXAMPLE 2

Preparation of S-methyl N-[{N-methyl-N-(N,N-bis(ethoxycarbonylethyl)aminosulfenyl)carbamoyl}oxy]thioacetamidate To 50 ml of methylene chloride was added 8.1 g (0.05 mole) of S-methyl N-[(methylcarbamoyl)oxy]thioacetamidate and 14.2 g (0.05 mole) of N,N-bis(ethoxycarbonylethyl)aminosulfonyl chloride, and the mixture was cooled to 0° to 5° C. 6 g (0.06 mole) of triethylamine was dropwise added thereto at the same temperature, and the resulting mixture was stirred for 2 hours. After completion of the reaction, the reaction solution was washed successively with water, diluted hydrochloric acid and water, and the methylene chloride layer was dried and concentrated. To the concentrated residue was added diethyl ether, and crystals were filtered off. Then, the ethereal layer was concentrated to obtain an oily product. Yield: 15.4 g (75.3%).

For the identification of the product, a portion thereof was purified by silica gel column chromatography, using benzene/ethyl acetate (4:1) as the elution solvent, whereby an oily product was obtained.

Elemental Analysis:

|  | C | H | N |
|---|---|---|---|
| Found (%) | 44.12 | 6.79 | 10.05 |
| Calcd. for $C_{15}H_{27}N_3O_6S_2$ (molecular wt. 409.537) | 43.99 | 6.65 | 10.26 |

NMR in $CDCl_3$:
$\delta$1.25 ppm (t, 3H), $\delta$2.27 ppm (s, 3H),
$\delta$2.38 ppm (s, 3H), $\delta$2.64 ppm (t, 4H),
$\delta$3.37 ppm (s, 3H), $\delta$3.40 ppm (t, 4H),
$\delta$4.07 ppm (q, 4H).

Thus, the product was confirmed to have the following formula:

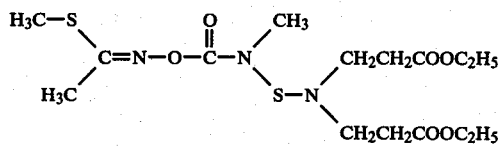

EXAMPLES 3 TO 20

The compounds shown in Table 1 below were prepared in the same manner as in Example 1 or 2. The structures, physical properties and NMR data of these compounds are also shown in Table 1.

TABLE 1

| Example No. | Structure | Physical Properties | NMR Data [δ Value (ppm) in CDCl₃] |
|---|---|---|---|
| 3 | H₃C—S\C=N—O—C(=O)—N(CH₃)—S—N(CH₂CH₂CH₂CH₃)(CH₂COOC₂H₅) / H₃C | Oily product | δ0.7–2.0 (m, 10H)<br>δ2.29 (s, 3H)<br>δ2.40 (s, 3H)<br>δ3.1–3.7 (m, 2H)<br>δ3.40 (s, 3H)<br>δ4.13 (s, 2H)<br>δ4.15 (q, 2H) |
| 4 | H₃C—S\C=N—O—C(=O)—N(CH₃)—S—N(CH₂CH₂CH₃)(CH₂CH₂COOC₂H₅) / H₃C | Oily product | δ0.8–2.0 (m, 5H)<br>δ1.27 (t, 3H)<br>δ2.27 (s, 3H)<br>δ2.39 (s, 3H)<br>δ2.70 (t, 2H)<br>δ3.0–3.6 (m, 4H)<br>δ3.40 (s, 3H)<br>δ4.10 (q, 2H) |
| 5 | H₃C—S\C=N—O—C(=O)—N(CH₃)—S—N(CH₂CH₂CH₂CH₃)(CH₂CH₂COOCH₃) / H₃C | Oily product | δ0.7–2.0 (s, 7H)<br>δ2.27 (s, 3H)<br>δ2.38 (s, 3H)<br>δ2.65 (t, 2H)<br>δ2.9–3.5 (m, 4H)<br>δ3.38 (s, 3H)<br>δ3.64 (s, 3H) |
| 6 | H₃C—S\C=N—O—C(=O)—N(CH₃)—S—N(CH₂CH(CH₃)₂)(CH₂CH₂COOC₂H₅) / H₃C | Oily product | δ0.85 (d, 6H)<br>δ1.20 (t, 3H)<br>δ1.6–2.2 (m, 1H)<br>δ2.64 (t, 2H)<br>δ2.28 (s, 3H)<br>δ2.39 (s, 3H)<br>δ3.0–3.6 (m, 4H)<br>δ3.39 (s, 3H)<br>δ4.07 (q, 2H) |
| 7 | H₃C—S\C=N—O—C(=O)—N(CH₃)—S—N(cyclohexyl)(CH₂CH₂COOC₂H₅) / H₃C | Oily product | δ0.8–2.0 (m, 10H)<br>δ1.20 (t, 3H)<br>δ2.22 (s, 3H)<br>δ2.36 (s, 3H)<br>δ2.60 (t, 2H)<br>δ3.0–3.5 (m, 3H)<br>δ3.37 (s, 3H)<br>δ4.05 (q, 2H) |
| 8 | H₃C—S\C=N—O—C(=O)—N(CH₃)—S—N(CH₂—C₆H₅)(CH₂CH₂COOC₂H₅) / H₃C | Oily product | δ1.24 (t, 3H)<br>δ2.27 (s, 3H)<br>δ2.37 (s, 3H)<br>δ2.64 (t, 2H)<br>δ3.0–3.4 (m, 2H)<br>δ3.39 (s, 3H)<br>δ4.08 (q, 2H)<br>δ4.43 (s, 2H)<br>δ7.21 (s, 5H) |
| 9 | H₃C—S\C=N—O—C(=O)—N(CH₃)—S—N(4-Cl-C₆H₄)(CH₂CH₂COOC₂H₅) / H₃C | Oily product | δ1.23 (t, 3H)<br>δ2.29 (s, 3H)<br>δ2.40 (s, 3H)<br>δ2.66 (t, 2H)<br>δ3.0–3.5 (m, 2H)<br>δ3.40 (s, 3H)<br>δ4.10 (q, 2H)<br>δ5.8–7.7 (m, 4H) |
| 10 | H₃C—S\C=N—O—C(=O)—N(CH₃)—S—N(3-CH₃-C₆H₄)(CH₂CH₂COOC₂H₅) / H₃C | Oily product | δ1.25 (t, 3H)<br>δ2.27 (s, 3H)<br>δ2.34 (s, 3H)<br>δ2.37 (s, 3H)<br>δ2.65 (t, 2H)<br>δ3.0–3.4 (m, 2H)<br>δ3.40 (s, 3H)<br>δ4.08 (q, 2H)<br>δ6.5–7.7 (m, 4H) |

TABLE 1-continued

| Example No. | Structure | Physical Properties | NMR Data [δ Value (ppm) in CDCl₃] |
|---|---|---|---|
| 11 | H₃C—S\C=N—O—C(=O)—N(CH₃)—S—N(CH₂COOC₂H₅)(CH₂COOC₂H₅), H₃C | Oily product | δ1.26 (t, 6H)<br>δ2.28 (s, 3H)<br>δ2.40 (s, 3H)<br>δ3.40 (s, 3H)<br>δ4.19 (q, 4H)<br>δ4.30 (s, 4H) |
| 12 | H₃C—S\C=N—O—C(=O)—N(CH₃)—S—N(COOC₂H₅)(CH₂COOC₂H₅), H₃C | Oily product | δ1.25 (t, 3H)<br>δ1.29 (t, 3H)<br>δ2.27 (s, 3H)<br>δ2.40 (s, 3H)<br>δ3.39 (s, 3H)<br>δ4.02 (q, 2H)<br>δ4.07 (q, 2H)<br>δ4.27 (s, 2H) |
| 13 | H₃C—S\C=N—O—C(=O)—N(CH₃)—S—N(COCH₂CH₃)(CH₂COOC₂H₅), H₃C | Oily product | δ1.15 (t, 3H)<br>δ1.23 (t, 3H)<br>δ2.27 (s, 3H)<br>δ2.7–3.3 (m, 2H)<br>δ2.39 (s, 3H)<br>δ3.39 (s, 3H)<br>δ4.11 (q, 2H)<br>δ4.41 (s, 2H) |
| 14 | H₃C—S\C=N—O—C(=O)—N(CH₃)—S—N(SO₂-C₆H₄-CH₃)(CH₂COOC₂H₅), H₃C | Oily product | δ1.20 (t, 3H)<br>δ2.27 (s, 3H)<br>δ2.37 (s, 3H)<br>δ2.40 (s, 3H)<br>δ3.41 (s, 3H)<br>δ4.05 (q, 2H)<br>δ4.45 (s, 2H)<br>δ6.5–7.9 (m, 4H) |
| 15 | H₃C—S\C=N—O—C(=O)—N(CH₃)—S—N(CH(CH₃)₂)(CH₂CH₂COOC₄H₉), H₃C | Oily product | δ0.7–2.0 (m, 7H)<br>δ1.16 (d, 6H)<br>δ2.28 (s, 3H)<br>δ3.38 (s, 3H)<br>δ2.75 (t, 2H)<br>δ3.30 (s, 3H)<br>δ3.0–3.9 (m, 2H)<br>δ4.02 (m, 2H) |
| 16 | H₃C—S\C=N—O—C(=O)—N(CH₃)—S—N(CH₂CH₂CH₂CH₂CH₂CH₃)(CH₂CH₂COOC₂H₅), H₃C | Oily product | δ0.6–2.0 (m, 11H)<br>δ1.23 (t, 3H)<br>δ2.25 (s, 3H)<br>δ2.36 (s, 3H)<br>δ2.68 (t, 2H)<br>δ2.9–3.5 (m, 4H)<br>δ3.31 (s, 3H)<br>δ4.06 (q, 2H) |
| 17 | H₃C—S\C=N—O—C(=O)—N(CH₃)—S—N(CH(CH₃)₂)(CH₂CH₂COO-2-ethylhexyl), H₃C | Oily product | δ0.6–1.8 (m, 15H)<br>δ1.16 (d, 6H)<br>δ2.28 (s, 3H)<br>δ2.38 (s, 3H)<br>δ2.68 (t, 2H)<br>δ3.1–3.7 (m, 3H)<br>δ3.36 (s, 3H)<br>δ3.5–4.0 (m, 2H) |
| 18 | H₃C—S\C=N—O—C(=O)—N(CH₃)—S—N(n-octyl)(CH₂CH₂COOC₂H₅), H₃C | Oily product | δ0.6–1.8 (m, 15H)<br>δ1.20 (t, 3H)<br>δ2.26 (s, 3H)<br>δ2.39 (s, 3H)<br>δ2.69 (t, 2H)<br>δ3.0–3.6 (m, 4H)<br>δ3.34 (s, 3H)<br>δ4.08 (q, 2H) |

TABLE 1-continued

| Example No. | Structure | Physical Properties | NMR Data [δ Value (ppm) in CDCl₃] |
|---|---|---|---|
| 19 | 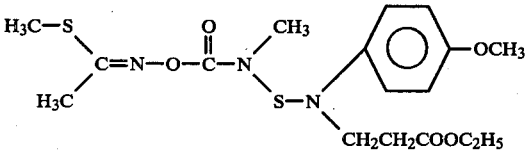 | Oily product | δ1.24 (t, 3H)<br>δ2.26 (s, 3H)<br>δ2.38 (s, 3H)<br>δ2.68 (t, 2H)<br>δ3.0–3.5 (m, 2H)<br>δ3.32 (s, 3H)<br>δ3.54 (s, 3H)<br>δ4.05 (q, 2H)<br>δ6.9–7.4 (m, 4H) |
| 20 | 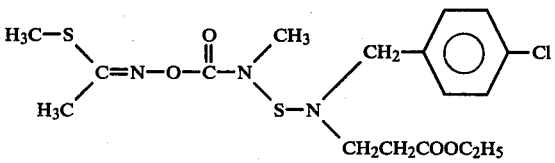 | Oily product | δ1.23 (t, 3H)<br>δ2.28 (s, 3H)<br>δ2.38 (s, 3H)<br>δ2.69 (t, 2H)<br>δ3.0–3.6 (m, 2H)<br>δ3.36 (s, 3H)<br>δ4.04 (q, 2H)<br>δ4.42 (s, 2H)<br>δ6.8–7.4 (m, 4H) |

Preparation Examples of this invention are given below. These prescriptions are applicable to all the compounds of this invention; a suitable prescription is usable for a particular application. The prescriptions are shown only for illustrative purposes, and the proportions of the active component, organic solvent, surfactant and carrier are variable as desired. In some cases, the kinds of organic solvent, surfactant, carrier, etc., can also be changed. The percentages are all by weight.

PREPARATION EXAMPLE 1

50% Wettable Powder:

| | |
|---|---|
| Compound of Example 7 | 50.0% |
| Kaolin | 30.0 |
| Talc | 10.0 |
| Alkyl sulfate | 5.5 |
| Condensate of naphthalenesulfonic acid and formaldehyde | 3.5 |
| Alkyl phosphate | 1.0 |

These ingredients were uniformly mixed with stirring using a Shinagawa-type mixer. The mixture was then finely pulverized using a ball mill to obtain a wettable powder.

PREPARATION EXAMPLE 2

50% Emulsion:

| | |
|---|---|
| Compound of Example 2 | 50.0% |
| Xylene | 30.0 |
| Cyclohexanone | 10.0 |
| Polyoxyethylene sorbitan monooleate | 6.5 |
| Sorbitan monooleate | 3.5 |

These ingredients were uniformly mixed and dissolved to obtain an emulsion.

PREPARATION EXAMPLE 3

20% Granule:

| | |
|---|---|
| Wettable powder of Preparation Example 1 | 40.0% |
| Dolomite | 60.0 |

These ingredients were uniformly mixed, a 2% aqueous solution of carboxymethyl cellulose was added to the mixture in an amount of 15 parts by weight per 100 parts by weight of the mixture, and the resulting mixture was thoroughly kneaded. The mixture was then granulated using a granulator and finely cleaved, followed by drying it to obtain a granule.

Test Examples are given below.

TEST EXAMPLE 1

Ten third-instar larvae of tobacco cutworm (*Spodoptera litura*) were placed on a cabbage (one-month-old seedlings) planted in a pot, and a 50% emulsion of the compound to be tested was diluted to a specified concentration and applied to the leaves of the plant to fully wet them. The test compound of each specified concentration was tested on two pots. Three days later, the larvae were checked for mortality, with the results listed in Table 2, which also shows the results achieved for control groups and untreated groups for comparison.

TABLE 2

| Test Compound (Example No.) | Mortality (%) Concentration of Active Ingredient (ppm) | | |
|---|---|---|---|
| | 400 | 200 | 100 |
| 1 | 100 | 90 | 85 |
| 2 | 100 | 100 | 75 |
| 3 | 100 | 100 | 100 |
| 4 | 100 | 100 | 100 |
| 5 | 100 | 100 | 100 |
| 6 | 100 | 95 | 70 |
| 7 | 100 | 100 | 95 |
| 8 | 100 | 100 | 100 |
| 9 | 100 | 70 | 50 |
| 10 | 100 | 85 | 60 |
| 11 | 100 | 75 | 45 |
| 12 | 100 | 100 | 100 |
| 13 | 100 | 90 | 75 |
| 14 | 100 | 80 | 60 |
| 15 | 100 | 95 | 75 |
| 16 | 100 | 80 | 70 |
| 17 | 100 | 70 | 50 |
| 18 | 100 | 75 | 60 |
| 19 | 100 | 80 | 75 |
| 20 | 100 | 80 | 75 |
| Control* | 100 | 100 | 80 |
| Untreated | | 0 | |

*S—Methyl N—[(methylcarbamoyl)oxy]thioacetamidate was used as the control.

TEST EXAMPLE 2

An emulsion of specified concentration was prepared from a 50% wettable powder of the compound to be tested and applied to the leaves of paddy rice (one-month-old seedlings) planted in a pot to fully wet the leaves. After air-drying the emulsion, the pot was covered with a net cage, into which 10 female adults of green rice leafhopper (*Nephotettix cincticeps*) were released. The compound of each specified concentration was tested on two pots. Three days later, the insects were checked for mortality, with the results listed in Table 3, which also shows the results achieved for control groups and untreated groups for comparison.

TABLE 3

| Test Compound | Mortality (%) Concentration of Active Ingredient (ppm) | | |
|---|---|---|---|
| (Example No.) | 800 | 400 | 200 |
| 1 | 100 | 80 | 60 |
| 2 | 100 | 95 | 60 |
| 3 | 100 | 100 | 80 |
| 4 | 100 | 100 | 95 |
| 5 | 100 | 100 | 95 |
| 6 | 100 | 90 | 80 |
| 7 | 100 | 100 | 65 |
| 8 | 100 | 100 | 75 |
| 9 | 100 | 100 | 70 |
| 10 | 100 | 100 | 90 |
| 11 | 100 | 80 | 60 |
| 12 | 100 | 100 | 80 |
| 13 | 100 | 100 | 75 |
| 14 | 100 | 100 | 80 |
| 15 | 100 | 100 | 80 |
| 16 | 100 | 100 | 75 |
| 17 | 100 | 90 | 75 |
| 18 | 100 | 90 | 75 |
| 19 | 100 | 100 | 80 |
| 20 | 100 | 100 | 80 |
| Control* | 100 | 100 | 90 |
| Untreated | | 0 | |

*S—Methyl N—[(methylcarbamoyl)oxy]thioacetamidate was used as the control.

TEST EXAMPLE 3

Granules containing 10% of the compound to be tested were mixed, in a specified amount, with soil contaminated with larvae of southern root-knot nematode (*Meloidogyne incognita*), and tomato seedlings were immediately transplanted in the soil. One month later, the roots of the plant were checked for the formation of nodules. Two test areas, 2×2 m² each, were used for the compound as applied in each specified amount. The degree of formation of the nodules was determined according to the criteria given below, with the results listed in Table 4, which also shows the results achieved for control groups and untreated groups for comparison.

Degree of formation of nodules:
0: 0%,
1: 1 to 24%,
2: 25 to 49%,
3: 50 to 74%,
4: 75 to 100%,

TABLE 4

| Test Compound | Degree of Formation of Nodules Amount of Granules Aplied (kg/10 a) | | |
|---|---|---|---|
| (Example No.) | 50 | 25 | 10 |
| 1 | 1 | 3 | 3 |
| 2 | 2 | 3 | 3 |
| 3 | 1 | 2 | 2 |
| 4 | 1 | 2 | 3 |
| 5 | 1 | 2 | 2 |
| 6 | 2 | 3 | 3 |
| 7 | 1 | 3 | 4 |
| 8 | 2 | 2 | 4 |
| 9 | 2 | 2 | 4 |
| 10 | 2 | 2 | 3 |
| 11 | 2 | 4 | 4 |
| 12 | 1 | 3 | 3 |
| 13 | 1 | 3 | 4 |
| 14 | 1 | 2 | 4 |
| 15 | 2 | 3 | 3 |
| 16 | 2 | 3 | 4 |
| 17 | 2 | 4 | 4 |
| 18 | 2 | 3 | 4 |
| 19 | 1 | 3 | 3 |
| 20 | 2 | 2 | 3 |
| Control* | 2 | 4 | 4 |
| Untreated | | 4 | |

*Bis(2-chloro-1-methylethyl)ethane was used as the control.

TEST EXAMPLE 4

The compound to be tested was dissolved in a predetermined amount of acetone. The solution was diluted to various concentrations and locally applied to house fly (*Musca domestica*). Table 5 shows $LD_{50}$ values determined by the Probit method from the mortality 24 hours later.

TABLE 5

| Test Compound (Example No.) | $LD_{50}$ (µg/g) |
|---|---|
| 1 | 16.0 |
| 2 | 23.0 |
| 3 | 8.5 |
| 4 | 11.0 |
| 5 | 5.0 |
| 6 | 7.6 |
| 7 | 18.3 |
| 8 | 35.2 |
| 9 | 14.0 |
| 10 | 29.5 |
| 11 | 47.3 |
| 12 | 28.7 |
| 13 | 14.4 |
| 14 | 33.3 |
| 15 | 21.3 |
| 16 | 32.5 |
| 17 | 42.4 |
| 18 | 35.6 |
| 19 | 20.1 |
| 20 | 18.9 |
| Control* | 6.8 |

*S—Methyl N—[(methylcarbamoyl)oxy]thioacetamidate was used as the control.

TEST EXAMPLE 5

The compound to be tested was evaluated in terms of acute toxicity by oral administration against male mice. Table 6 shows $LD_{50}$ values determined by the Litchfield-Wilcoxon method from the mortality on the seventh day.

TABLE 6

| Test Compound (Example No.) | $LD_{50}$ (mg/kg) |
|---|---|
| 1 | 150 |
| 2 | 300 |
| 3 | 170 |
| 4 | 150 |
| 5 | 150 |
| 6 | 170 |

TABLE 6-continued

| Test Compound (Example No.) | LD$_{50}$ (mg/kg) |
| --- | --- |
| 7 | 200 |
| 8 | 250 |
| 9 | 250 |
| 10 | 250 |
| 11 | 300 |
| 12 | 200 |
| 13 | 200 |
| 14 | 250 |
| 15 | 280 |
| 16 | 300 |
| 17 | 300 |
| 18 | 270 |
| 19 | 250 |
| 20 | 250 |
| Control* | 16 |

*S—Methyl N—[(methylcarbamoyl)oxy]thioacetamidate was used as the control.

While the invention has been described in detail and with reference to specific embodiments thereof, it will be apparent to one skilled in the art that various changes and modifications can be made therein without departing from the spirit and scope thereof.

What is claimed is:

1. An S-methyl N-[{N-methyl-N-(N,N-disubstituted aminosulfenyl)carbamoyl}oxy]thioacetamidate derivative represented by the formula (I):

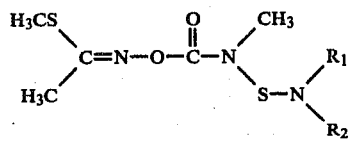

wherein $R_1$ and $R_2$, which may be the same or different, each represents $-X-COOR_3$, in which X represents an alkylene group having 1 to 6 carbon atoms, and $R_3$ represents an alkyl group having 1 to 8 carbon atoms or a cycloalkyl group having 3 to 6 carbon atoms; $R_2$ further represents an alkyl group having 1 to 8 carbon atoms; a cycloalkyl group having 3 to 6 carbon atoms; a phenyl group which may be substituted with a halogen atom, an alkyl group having 1 to 3 carbon atoms or an alkoxy group having 1 to 3 carbon atoms; a benzyl group which may be substituted with a halogen atom, an alkyl group having 1 to 3 carbon atoms or an alkoxy group having 1 to 3 carbon atoms; or $-Z-R_4$, in which Z represents a carbonyl group or a sulfonyl group, and $R_4$ represents an alkyl group having 1 to 3 carbon atoms, an alkoxy group having 1 to 3 carbon atoms or a phenyl group which may be substituted with a lower alkyl group.

2. An insecticidal, miticidal or nematocidal composition comprising an insecticidally, miticidally or nematocidally effective amount of the S-methyl N-[{N-methyl-N-(N,N-disubstituted aminosulfenyl)carbamoyl}oxy]thioactamidate derivative according to claim 1 as an active ingredient.

3. A method for controlling noxious insects, mites or nematodes by applying thereto an effective amount of the S-methyl N-[{N-methyl-N-(N,N-disubstituted aminosulfenyl)carbamoyl}-oxy]thioacetamidate derivative according to claim 1.

* * * * *